(12) United States Patent
Chang et al.

(10) Patent No.: US 11,806,446 B2
(45) Date of Patent: *Nov. 7, 2023

(54) ODOR BARRIER FILM

(71) Applicant: Hollister Incorporated, Libertyville, IL (US)

(72) Inventors: Moh-Ching Oliver Chang, Lake in the Hills, IL (US); George J. Cisko, Spring Grove, IL (US)

(73) Assignee: Hollister Incorporated, Libertyville, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/858,510

(22) Filed: Jul. 6, 2022

(65) Prior Publication Data

US 2022/0331497 A1   Oct. 20, 2022

Related U.S. Application Data

(63) Continuation of application No. 16/589,980, filed on Oct. 1, 2019, now Pat. No. 11,406,741, which is a
(Continued)

(51) Int. Cl.
| | |
|---|---|
| *A61L 28/00* | (2006.01) |
| *A61F 5/441* | (2006.01) |
| *B32B 27/30* | (2006.01) |
| *B32B 1/08* | (2006.01) |
| *B32B 27/08* | (2006.01) |

(Continued)

(52) U.S. Cl.
CPC .......... *A61L 28/0015* (2013.01); *A61F 5/441* (2013.01); *A61F 5/445* (2013.01); *A61L 28/0011* (2013.01); *B32B 1/08* (2013.01); *B32B 27/08* (2013.01); *B32B 27/30* (2013.01); *B32B 27/302* (2013.01); *B32B 27/306* (2013.01); *B32B 27/308* (2013.01); *B32B 27/32* (2013.01); *B32B 27/34* (2013.01); *B32B 2250/24* (2013.01); *B32B 2307/54* (2013.01);
(Continued)

(58) Field of Classification Search
CPC .......... A61F 5/445; A61F 5/44; A61F 5/4405; B32B 27/32; B32B 27/08; B32B 27/30; B32B 27/306; B32B 27/308; B32B 27/34; B32B 27/302; C08L 77/00
See application file for complete search history.

(56) References Cited

U.S. PATENT DOCUMENTS

| | | | | |
|---|---|---|---|---|
| 4,239,826 A | * | 12/1980 | Knott, II | ............... B32B 27/306 428/522 |
| 4,254,169 A | * | 3/1981 | Schroeder | ............... B32B 27/08 428/522 |

(Continued)

FOREIGN PATENT DOCUMENTS

| | | |
|---|---|---|
| DE | 4100350 A1 | 4/1992 |
| EP | 0588667 A2 | 3/1994 |

(Continued)

*Primary Examiner* — Guy K Townsend
(74) *Attorney, Agent, or Firm* — Levenfeld Pearlstein, LLC

(57) ABSTRACT

A multilayer film for ostomy and bowel management applications includes a barrier layer comprising at least about 90% wt. nylon 6/69. The multilayer film provides excellent mechanical and odor barrier properties, and softness and quietness desired in ostomy and bowel management applications.

18 Claims, 3 Drawing Sheets

Related U.S. Application Data continuation of application No. 14/989,535, filed on Jan. 6, 2016, now Pat. No. 10,500,315, which is a continuation of application No. 13/780,398, filed on Feb. 28, 2013, now Pat. No. 9,265,648.

(60) Provisional application No. 61/647,222, filed on May 15, 2012.

(51) Int. Cl.
 *B32B 27/32* (2006.01)
 *B32B 27/34* (2006.01)
 *A61F 5/445* (2006.01)

(52) U.S. Cl.
 CPC ... *B32B 2307/7248* (2013.01); *B32B 2439/80* (2013.01); *B32B 2535/00* (2013.01); *B32B 2597/00* (2013.01)

(56) References Cited

U.S. PATENT DOCUMENTS

| | | | | |
|---|---|---|---|---|
| 4,909,726 A * | 3/1990 | Bekele | | B32B 7/12 428/34.3 |
| 4,983,171 A * | 1/1991 | Schirmer | | A61F 5/445 D24/118 |
| 5,346,959 A * | 9/1994 | Goman (Gomez) | | C08L 83/12 524/910 |
| 5,567,489 A * | 10/1996 | Allen | | A61K 9/703 604/338 |
| 5,895,694 A * | 4/1999 | Zavadsky | | B32B 27/18 428/476.3 |
| 6,143,383 A * | 11/2000 | Giori | | A61L 28/0015 428/476.3 |
| 6,258,423 B1 * | 7/2001 | Giori | | B32B 27/36 428/347 |
| 6,261,698 B1 * | 7/2001 | Broda | | B32B 27/08 428/476.3 |
| 6,455,161 B1 * | 9/2002 | Regnier | | C08J 5/18 428/483 |
| 6,558,809 B1 * | 5/2003 | Kelch | | C08J 5/18 428/522 |
| 6,620,474 B1 * | 9/2003 | Regnier | | B32B 27/36 428/476.3 |
| 6,858,313 B2 * | 2/2005 | Musco | | B29C 48/10 428/34.3 |
| 6,884,480 B2 * | 4/2005 | Bradfute | | B32B 27/30 428/34.9 |
| 6,946,182 B1 * | 9/2005 | Allgeuer | | B29C 59/04 428/172 |
| 7,270,860 B2 * | 9/2007 | Giori | | B32B 27/32 428/34.1 |
| 7,815,617 B2 * | 10/2010 | Dircks | | B32B 37/12 604/332 |
| 7,819,849 B2 * | 10/2010 | Dircks | | B32B 7/12 604/332 |
| 7,915,186 B2 * | 3/2011 | Willis | | A61F 5/441 442/394 |
| 8,858,525 B2 * | 10/2014 | Bekele | | B32B 27/302 428/35.2 |
| 9,265,648 B2 * | 2/2016 | Chang | | B32B 27/302 |
| 9,301,869 B2 * | 4/2016 | Chang | | A61L 28/0015 |
| 9,895,255 B2 * | 2/2018 | Chang | | B32B 27/34 |
| 10,322,024 B2 * | 6/2019 | Chang | | B32B 27/08 |
| 10,470,917 B2 * | 11/2019 | Chang | | B32B 27/32 |
| 10,500,315 B2 * | 12/2019 | Chang | | B32B 27/30 |
| 10,980,661 B2 * | 4/2021 | Chang | | B32B 27/065 |
| 11,351,054 B2 * | 6/2022 | Chang | | B32B 5/32 |
| 11,406,741 B2 * | 8/2022 | Chang | | B32B 27/302 |
| 2002/0025394 A1 * | 2/2002 | Bradfute | | B32B 27/30 428/476.1 |
| 2003/0064182 A1 * | 4/2003 | Giori | | B32B 27/34 428/476.1 |
| 2004/0228992 A1 * | 11/2004 | Giori | | B32B 27/32 428/35.7 |
| 2005/0079372 A1 * | 4/2005 | Schmal | | B32B 27/32 428/482 |
| 2005/0203223 A1 * | 9/2005 | Ohyama | | C08L 77/06 524/100 |
| 2006/0177490 A1 * | 8/2006 | Massouda | | C08L 53/00 424/443 |
| 2006/0263596 A1 * | 11/2006 | Bamborough | | B32B 27/00 428/40.1 |
| 2007/0207186 A1 * | 9/2007 | Scanlon | | B29C 55/26 623/1.42 |
| 2007/0237916 A1 * | 10/2007 | Rasmussen | | A61F 5/441 428/521 |
| 2008/0038530 A1 * | 2/2008 | Rimondi | | B32B 27/325 428/220 |
| 2009/0061057 A1 * | 3/2009 | Beckwith | | B32B 27/32 426/546 |
| 2009/0061061 A1 * | 3/2009 | Beckwith | | B65D 65/22 426/546 |
| 2009/0061062 A1 * | 3/2009 | Beckwith | | B32B 27/306 426/546 |
| 2009/0123613 A1 * | 5/2009 | Hayes | | B32B 27/16 426/106 |
| 2009/0317611 A1 * | 12/2009 | Mueller | | B32B 7/02 53/562 |
| 2010/0121290 A1 * | 5/2010 | Rasmussen | | B32B 27/40 428/95 |
| 2010/0139707 A1 * | 6/2010 | Boonstra | | B32B 25/08 134/29 |
| 2011/0118679 A1 * | 5/2011 | Bekele | | B32B 27/32 604/408 |
| 2011/0125114 A1 * | 5/2011 | Bekele | | A61F 5/445 181/290 |
| 2011/0236540 A1 * | 9/2011 | Owensby | | B65D 81/343 426/106 |
| 2012/0197237 A1 * | 8/2012 | Holzbauer | | A61M 25/0045 604/540 |
| 2012/0232504 A1 * | 9/2012 | Chang | | A61F 5/445 428/476.1 |
| 2013/0310782 A1 * | 11/2013 | Chang | | B32B 27/308 604/333 |
| 2014/0205828 A1 * | 7/2014 | Chang | | B32B 27/304 428/317.1 |
| 2014/0207094 A1 * | 7/2014 | Chang | | B32B 27/302 604/339 |
| 2016/0114082 A1 * | 4/2016 | Chang | | B32B 27/30 604/333 |
| 2018/0125696 A1 * | 5/2018 | Chang | | B32B 27/306 |
| 2019/0231581 A1 * | 8/2019 | Chang | | B32B 5/32 |
| 2020/0030497 A1 * | 1/2020 | Chang | | A61F 5/445 |
| 2022/0331497 A1 * | 10/2022 | Chang | | B32B 1/08 |
| 2023/0130048 A1 * | 4/2023 | Ebrahimi | | B32B 27/32 428/218 |

FOREIGN PATENT DOCUMENTS

| | | | |
|---|---|---|---|
| EP | 0700777 B1 | 12/2000 | |
| WO | 9311938 A1 | 6/1993 | |
| WO | 2011056861 A1 | 5/2011 | |
| WO | WO-2011056861 A1 * | 5/2011 | ............. A61F 5/445 |

* cited by examiner

ODOR BARRIER FILM

CROSS-REFERENCE TO RELATED APPLICATION DATA

This application is a continuation application of U.S. application Ser. No. 16/589,980 filed Oct. 1, 2019, which is a continuation application of U.S. application Ser. No. 14/989,535 filed Jan. 6, 2016, which is a continuation application of U.S. application Ser. No. 13/780,398 filed Feb. 28, 2013, which claims the benefit of priority of Provisional U.S. Patent Application Serial No. 61/647,222, filed May 15, 2012 entitled, "ODOR BARRIER FILM."

BACKGROUND

The present disclosure relates to odor barrier materials, and more particularly to films and tubes having a layer of an odor barrier material for medical uses such as ostomy and bowel management applications.

Gas and odor barrier films are known and widely used in the medical and food packaging industries. Many such films have a barrier layer that contains chlorine; other barrier layers are chlorine-free. Chlorine-containing barrier layers use, for example, copolymers of vinylidene chloride vinyl chloride (VDC-VC) copolymers) and vinylidene chloride methyl acrylate copolymer (VDC-MA copolymers). These chlorine-containing films have exceptionally high malodor-causing compound barrier properties and are typically not adversely affected by the presence of moisture. One drawback to the use of chlorine-containing compounds is that these compounds, generally, present environmental issues in disposal, for example, incineration of materials after use. Another drawback is that specialized equipment is required to process these materials due to the corrosive nature of the chlorine compounds.

Barrier layers of chlorine-free material include vinyl alcohol based polymers, for example, ethylene vinyl alcohol (EVOH) copolymers and poly(vinyl alcohol) (PVOH). Unfortunately, these materials have been found to have reduced barrier performance in the presence of humidity.

Ostomy products and other applications relating to storing and transporting bodily waste are highly demanding and typically subject materials used in such products to high levels of moisture. At the same time, it is extremely important that the odor barrier properties of the material are and remain high throughout their useful life. In addition, it is imperative that the mechanical strength of the material is also high and remains high for a sufficiently long period of time for extended use of the product.

Other factors and properties that must also be considered in ostomy product use are the comfort of the material, as such products are worn next to the user's body, the flexibility of the material so that it conforms to the user's movements, and the quietness of the product so that wearing such a product is as audibly imperceptible as possible. The chlorine-containing materials possess these beneficial properties and qualities, but have the aforementioned environmental issues in disposal and processing.

In an effort to provide a film having the beneficial properties and characteristics of VDC-VC, VDC-MA and other chlorine-containing materials, without the detrimental effects of these chlorine-containing materials, various layered films have been composed of non-chlorine containing materials. One known film, disclosed in DE-A-4100350, is a seven layer chlorine-free film for packaging material for infusion solutions. The material is composed of a base material that is a coextruded film made of an ethylene-vinyl alcohol (EVOH) copolymer and two coating polyethylene (PE) layers onto which a PE layer and an EVOH copolymer layer are extrusion laminated.

One film used in food packaging, disclosed in EP-A-0588667, is a multiple layer film, moisture barrier material that includes a core layer made of an oxygen barrier material, such as an EVOH copolymer, two intermediate layers provided on the core layer of a propylene (PP) polymer or copolymer or a polymeric adhesive, such as a carboxylic acid or maleic anhydride-modified polyolefin such as polypropylene-based carboxylic acid or maleic anhydride-modified polyolefin. Moisture barrier layers are provided as a blend of a PP polymer or copolymer and a hydrocarbon resin, and outermost layers covering the outer surfaces are also PP polymer or copolymer.

One film used in the manufacture of ostomy pouches, disclosed in International application publication WO93/11938, is a five-layer barrier structure having a gas barrier layer, two moisture barrier layers and optionally one or more adhesive layers disposed therebetween. The moisture barrier layer is a mesophase PP-based material which contacts one or both of the sides of the gas barrier layer. The gas barrier layer is made of an EVOH copolymer.

Other multi-layer films, such as those disclosed in U.S. Pat. Nos. 4,239,826 and 4,254,169, which include an oxygen barrier layer formed of vinyl alcohol polymer or copolymers (e.g. PVOH, EVOH), and moisture barrier layers formed of partially hydrolyzed vinyl acetate polymer or copolymer, or modified polyolefins, are also known. Such films have been found to be useful in the manufacture of food packaging containers.

A five layer chlorine-free ostomy pouch film is also known. Such a film, which is disclosed in Giori, U.S. Pat. No. 7,270,860 and is incorporated herein in its entirety by reference, has a core odor barrier layer formed of a blend or a compound including amorphous polyamide, and anhydride-modified olefin polymer or copolymer. The film also includes two tie layers on both sides of the core layer and two EVA or EVA-based surface layers.

Still another film, disclosed in EP 0700777 B 1, is a chlorine-free composition having a gas-barrier layer of a non-chlorine containing organic polymer which is substantially impermeable to oxygen, two tie layers each contacting one side of the barrier layer, an inner surface layer, an outer surface layer and two intermediate layers positioned between the surface layers and tie layers. The intermediate layers are an ethylene-propylene copolymer having a flexural modulus (measured according to ASTM D-882) of less than 200 MPa., preferably less than 150 MPa.

Multilayer films for ostomy applications including a barrier layer comprising amorphous polyamide also have been developed. For example, WO 2011/056861, which is commonly assigned to the assignee of the present application and incorporated in its entirety by reference, discloses such a multilayer film. The disclosed multilayer film is chlorine free, and thus, achieves the desired goal with respect to environmental safety. Further, it provides a better combination of physical properties, including moisture and odor barrier characteristics, tear strength, comfort and "quietness" when compared to other chlorine free films. However, some characteristics of amorphous polyamide, such as its high rigidity and high temperature requirements for extrusion, have presented manufacturing challenges in making and converting the multilayer film. For example, when coextruding the multilayer film including amorphous polyamide, high extrusion temperature for the amorphous polyamide can damage other layers, such as layers comprising EVA. Further, the hardness of the amorphous polyamide makes it tougher to cut the film and wears cutting knives quickly.

Accordingly, there is a need for a chlorine-free, multi-layer film for use in ostomy and continence products that provides a barrier for malodor causing compounds, which has more manufacturing friendly properties. Desirably, such a film and products made therefrom maintain high barrier performance characteristics even in high moisture applications, for prolonged periods of time. More desirably still, such a film and products made therefrom exhibit high tear strength, and the products exhibit "quietness" when in use.

BRIEF SUMMARY

Odor barrier materials, multilayer films, and tubes for ostomy and bowel management applications are provided according to various embodiments. Such materials, films and tubes include a barrier layer formed essentially from nylon 6/69 to provide excellent mechanical and odor barrier properties along with softness and quietness desired in ostomy and bowel management applications.

In one aspect, a multi-layer, chlorine-free film for ostomy and bowel management applications is provided. The film includes a barrier layer having first and second sides and respectively adjacent first and second outer layers. The barrier layer includes a low melt polyamide resin having a melting temperature between about 125° C. and about 135° C. present in a concentration of about 90% to about 100% by weight (% wt.) of the barrier layer. The barrier layer is substantially impermeable to malodor causing compounds. Each outer layer is formed from an ethylene vinyl acetate or ethylene methyl acrylate copolymer and blends thereof, or polypropylene-based resins and blends thereof. Each outer layer is arranged on a respective side of the barrier layer.

In one embodiment, the film includes first and second tie layers, each of which is arranged to contact a side of the barrier layer. The tie layers are formed from a maleic anhydride grafted resin. The resin is one or more of an ethylene-based copolymer, a propylene-based copolymer, an ethylene-octene polymer and a styrene block copolymer. Further, the film can also include first and second inner layers. The inner layers are formed from one of an ethylene propylene copolymer (polypropylene elastomer) based resin, an ethylene-octene based resin and blends thereof. Each inner layer is arranged to contact a respective tie layer, and each outer layer contacts a respective inner layer.

In some embodiments, the barrier layer is formed from about 100% wt. nylon 6/69. In other embodiments, the barrier layer includes about 90% wt. to about 99% wt. nylon 6/69 and about 1% wt. to about 10% wt. amorphous polyamide. For example, the barrier layer can include about 98% wt. nylon 6/69 and about 2% wt. amorphous polyamide.

Further, the thickness of the barrier layer is about 30% to 70% of a total thickness of the film. In one embodiment, a total thickness of the film is between about 60 μm and about 300 μm, and a thickness of the barrier layer is between about 25 μm and about 90 μm.

In another aspect, an ostomy pouch formed of a film made according to any of the above discussed embodiments is provided. The ostomy pouch includes two side walls, each of which is formed from the film. The ostomy pouch also includes a stoma-receiving opening on one of the side walls. The two side walls are sealed together along peripheral edges of the side walls to from the ostomy pouch.

In yet another aspect, a bowel management tube formed of a film made according to above discussed embodiments and having a total thickness between about 230 μm and 270 μm is provided. The film includes a barrier layer having a thickness between about 60 μm and about 80 μm.

In another aspect, an ostomy pouch formed of a multilayer film is provided. The multilayer film includes a barrier layer having first and second sides, first and second tie layers, and first and second outer layers. The barrier layer includes a low melt polyamide resin having a melting temperature between about 125° C. and about 135° C. present in a concentration of about 90% to about 100% by weight (% wt.) of the barrier layer. The barrier layer is substantially impermeable to malodor causing compounds. The tie layers are formed from a maleic anhydride grafted resin. The resin is one or more of an ethylene-based copolymer, a propylene-based copolymer, an ethylene-octene polymer and a styrene block copolymer. Each outer layer is formed from an ethylene vinyl acetate or ethylene methyl acrylate copolymer and blends thereof, or polypropylene-based resins and blends thereof. Each tie layer is arranged between the barrier layer and a respective outer layer.

In one embodiment, the multilayer film is a five-layer film having a total thickness between about 90 μm and about 110 μm. The barrier layer has a thickness between about 35 μm and about 55 μm. In another embodiment, the multilayer film is a seven-layer film. The multilayer film includes first and second inner layers. The inner layers are formed from one of an ethylene propylene copolymer (polypropylene elastomer) based resin, an ethylene-octene based resin and blends thereof. Each inner layer is arranged between a respective tie layer and a respective outer layer. The seven-layer film has a total thickness between about 90 μm and about 110 μm, and the barrier layer has a thickness between about 35 μm and about 55 μm.

In some embodiments, the barrier layer is formed from about 100% wt. nylon 6/69. In other embodiments, the barrier layer includes about 95% wt. to about 99% wt. nylon 6/69 and about 1% wt. to about 5% wt. amorphous polyamide. Preferably, the thickness of the barrier layer makes up about 35% to 55% of the total thickness of the multilayer film.

Other aspects, objectives and advantages will become more apparent from the following detailed description when taken in conjunction with the accompanying drawings.

BRIEF DESCRIPTION OF THE DRAWINGS

The benefits and advantages of the present embodiments will become more readily apparent to those of ordinary skill in the relevant art after reviewing the following detailed description and accompanying drawings, wherein.

DETAILED DESCRIPTION

Figure 1:
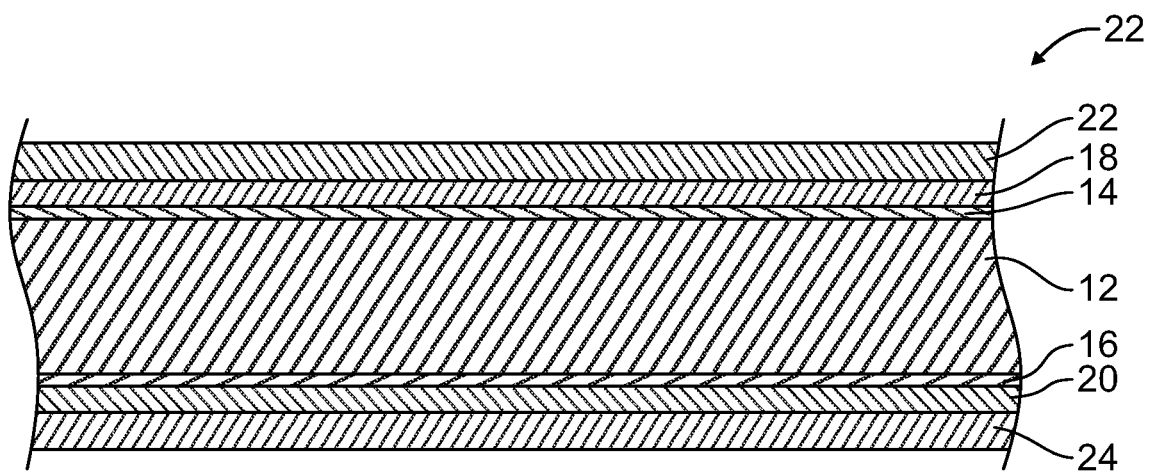
FIG. 1 is a cross-sectional illustration of a seven-layer film in accordance with an embodiment of the present disclosure.

While the present disclosure is susceptible of embodiment in various forms, there is shown in the drawings and will hereinafter be described a presently preferred embodiment with the understanding that the present disclosure is to be considered an exemplification and is not intended to limit the disclosure to the specific embodiment illustrated. The words "a" or "an" are to be taken to include both the singular and the plural. Conversely, any reference to plural items shall, where appropriate, include the singular.

Referring now to the figures and in particular to FIG. 1, there is shown a multilayer film 10 according to an embodiment. The film 10 includes a barrier layer 12 formed essentially from low-melt polyamide, preferably, nylon 6/69. The barrier layer is substantially impermeable to malodor causing compound typically encountered in ostomy pouches. Such malodor causing compounds can include sulfur containing compounds and indoles. Examples of sulfur-containing compounds include dimethyl disulfide, dimethyl trisulfide, diethyl disulfide, hydrogen sulfide and methyl mercaptan. Examples of indoles, and other malodor causing compounds include 3-methyl indole and methanethiol. Other compounds will be recognized by those skilled in the art. Further, the barrier layer imparts tear strength to the film, while at the same time facilitate achieving a "quite", e.g. low dB(A), film.

The film 10, as shown in FIG. 1, is a seven layer film. The barrier layer 12 is the thickest layer of the film 10, preferably making up more than about 25% of the total thickness, and more preferably between about 30% and 70% of the total thickness. On either side of the barrier layer 12 is a tie layer 14, 16. The tie layers facilitate adhesion of the barrier layer to the remainder of the film structure. First and second inner layers 18, 20 are present adjacent to the tie layers 14, 16, respectively. The inner layers provide added tear strength and quietness for the film in addition to those properties provide by the barrier film. The outermost layers are seal and skin layers 22, 24, that are adjacent the first and second inner layers 18, 20, respectively. The seal and skin layers provide good sealing characteristics (sealing by heat or other known methods to form a pouch or bag) and are also comfortable for application against a user's skin. The film thus has the structure ABCDCBA, where A represents the skin/seal layer, B represents the first and second inner layers, C represents the tie layers and D represents the barrier layer. Although the film 10 of this embodiment includes seven layers, in other embodiments, a multilayer barrier film can include more than seven layers or less than seven layers. For example, a multilayer film according to this disclosure can be a six-layer film including a barrier layer, two tie layers, an inner layer, and two skin layers (i.e. ABCDCA), or alternatively, a five-layer film including a barrier layer, two tie layers and two outer layers (i.e. ACDCA, BCDCB or ACDCB).

Barrier Layer

The barrier layer 12 is formed essentially from a low melt polyamide having a melting temperature lower than about 150° C., preferably about 125° C. to about 135° C. Preferably, the barrier layer 12 comprises at least 90% wt. nylon 6/69. Nylon 6/69 is an engineered thermoplastic polyamide, which is typically manufactured by the condensation of epsilon-capro-lactam, hexamethylenediamine and azelaic acid. Nylon 6/69 is also commonly referred to as PA 6/69. While it is believed that a variety of low melt polyamide resins may be used to form the barrier layer 12, effective results have been obtained with a nylon 6/69 resin marketed as Grilon® BM 13 SBG by EMS-Chemie of Sumter, SC Grilon® BM 13 SBG has a density of about 1.09 grams per cubic centimeter (g/cm$^3$) and a melting point of about 130° C.

The barrier layer 12 comprises nylon 6/69 in an amount greater than about 75% by weight, preferably greater than about 85% wt., and more preferably greater than about 95% wt. As shown in FIG. 1, the barrier layer 12 is the thickest layer of the film 10, which is configured to provide excellent odor barrier properties, mechanical (tear) strength and quietness to the film 10. In one preferred embodiment, the barrier layer 12 is formed from about 100% wt. nylon 6/69. In another embodiment, the barrier layer 12 is formed from a blend comprising about 95% wt. to 99.8% wt. nylon 6/69 and about 0.2% wt. to 5% wt. amorphous polyamide. Amorphous polyamide has a partially aromatic structure and is typically produced by the condensation of an aliphatic diamine with an aromatic diacid, or combination of diacids, in molar amounts equivalent to the diamine used. Partially aromatic nylons such as 6I/6T, MXDI/6I, MXD6/MXDI (wherein I is isophthalic acid, T is terephthalic acid, 6 is hexamethylenediamine, and MXD is metaxylenediamine) may also be mixed with nylon 6/69 to form the barrier layer 12.

While it is believed that a variety of amorphous polyamide resins may be used, effective results have been obtained with Grivory®, such as Grivory® G21, which is commercially available from EMS-Chemie of Sumter, SC Grivory® G21 has a density of about 1.18 g/cm$^3$ and a glass transition temperature (dry) of about 128° C. Another suitable amorphous nylon resin is Grivory® HB5299, which has a density of about 1.2 g/cm$^3$ and a glass transition temperature (dry) of about 95° C. and a melting point temperature of about 219° C. An alternative amorphous nylon, having similar properties a polyamide resin marketed as Selar®, such as Selar® PA3426, by DuPont Company. Selar® PA3426 is understood to be substantially amorphous with a density of about 1.19 g/cm$^3$ and a glass transition temperature (dry) of about 127° C. It has high melt strength and can be used under a broader range of processing conditions than conventional crystalline nylons.

Tie Layers

The tie layers 14, 16 can be formed of the same material or different materials. In the embodiment of FIG. 1, the tie layers 14, 16 are formulated from the same material. Suitable materials for the tie layers include, but not limited to, MAH grafted blend of EPR and PP (e.g. Zelas® MC721 AP from Mitsubishi); MAH grafted or copolymerized EMA, EVA, EBA, EEA or other polyolefins (e.g. Lotader® from Arkema, Bynel® from DuPont, Plexar® from Lyondellbassell); MAH grafted polypropylene (PP) concentrate (e.g. Bynel® from DuPont) blend with ethylene-propylene copolymer (PP-elastomer) (e.g. Vistamaxx® from Exxon, Versify® from Dow), ethylene-octene (EO) plastomer (e.g. Exact® from Exxon, Affinity® from Dow), EMA (e.g. Lotryl® from Arkema), or other polyolefins; or GMA grafted PE, EMA or other polyolefins (e.g. Lotader® from Arkema.) An olefin-based thermoplastic elastomer (EPR rubber), MAH grafted EMA copolymers, blends of EMA and MAH grafted linear low density polyethylene (LLDPE), PE, EVA copolymers, or ethylene modified with functional anhydride groups are believed particularly suitable.

One suitable material for the tie layers is a blend of about 80% of an EMA copolymer having methyl acrylate present at about 18.5% by weight of the copolymer and about 20% of a MAH grafted linear low density polyethylene (LLDPE), having maleic anhydride present at about 0.8% to 1.1% of the MAH-LLDPE polymer. One such EMA polymer is available from Arkema, Inc. as Lotryl®18MA02. This resin has a melting point temperature of 87° C. and a Shore D hardness of 30. One MAH grafted LLDPE is available from DuPont Company under the designation BynerCXA41E710.

Still another suitable material is a MAH grafted ethylene methyl acrylate copolymers (EMA) having maleic anhydride present at about 0.3% and methyl acrylate present at about 20% of the resin. One such material is available from Arkema, Inc as Lotader®4503, and has a melting point temperature of 78° C. and a Shore D hardness of 25.

Another suitable material for the tie layers is a MAH grafted blend of EPR and PP available as Zelas® MC721AP, from Mitsubishi Chemical Co. This resin has a melting point temperature of 158° C., a Shore A hardness of 75 and a specific gravity of 0.89. This resin imparts a high mechanical strength and serves to tie or adhere the barrier layer to the inner and skin/seal layers.

Still another material that is anticipated to be suitable is an epoxy functional rubber, such as the above-noted glycidyl methacrylate (GMA) copolymerized with ethylene and other monomers, such as E-MA-GMA (Lotader®AX8920) and E-GMA (Lotader®AX8840).

Inner Layers

The first and second inner layers, 18, 20 can be formulated from the same material or different materials. In the embodiment of FIG. 1, both of the first and second inner layers 18, 20 are formed of the same material. The inner layers 18, 20 impart added mechanical (tear) strength and quietness to the film 10. Ethylene based polymers, such as ethylene vinyl acetate (EVA) copolymer, ethylene-octene (EO) plastomers, and ethylene-propylene (EP) copolymers (PP-elastomer) are suitable film forming materials for the inner layers. One suitable material is an ethylene vinyl acetate (EVA) copolymer having a vinyl acetate content of about 8% to 30% and preferably about 10% to about 25%, a melting point temperature of about 86° C. and a Shore A hardness of about 91, such as Escorene®FL00218 and Escorene®UL00514, available from ExxonMobil Corporation.

Another suitable material is an EO plastomer having a melting point temperature of about 95° C. and specific gravity of about 0.902, such as Exact® 0203 resin, also available from ExxonMobil Corporation, which has a specific gravity of about 0.88 and a Shore A hardness of about 95. This resin is designed for both monolayer and multilayer co-extruded cast film applications and is suitable in applications that require toughness and sealing performance. Typical applications include film for industrial packaging.

Still another suitable resin is an ethylene-propylene copolymer (PP-elastomer) resin that exhibits a low melt flow rate making it suitable for film application and sealing. It has a low modulus and thus exhibits low noise characteristics. It has excellent compatibility with PP and PE. One such material is available from Dow Chemical from as Versify®2200. This resin has melting point of about 82° C., a Shore A hardness of 94 and a Shore D hardness of 42. It has a specific gravity of 0.878. Blends of various PP copolymer resins have also been found to be suitable, for example, blends of Versify®2200 and Versify®3400, which is a similar PP copolymer resin, but has a higher melting point of about 97° C., a Shore A hardness of 72 and a Shore D hardness of 22, and a specific gravity of about 0.865. Suitable blends can have ratios of about 50% of Versify®2200 to about 75% of Versify®2200 by weight of the blend. PP-elastomers such as Versify® from Dow, Vistamaxx® from Exxon, and Notio® from Mitsui are also suitable.

Seal/Skin Layers

The seal and skin layers 22, 24 can likewise be formed of the same or different materials. In the embodiment of FIG. 1, the seal/skin layers 22, 24 are formed of the same material. These layers are typically formed of an ethylene-based polymer or copolymer. Suitable resins include, for example, copolymers of ethylene with vinyl esters, such as vinyl acetate copolymer (EVA) and copolymers of ethylene methyl acrylate (EMA). EVA copolymers contain about 10% to 35% vinyl acetate and more preferably, about 18% by weight vinyl acetate, by weight of the copolymer, for example, EscoreneFL®00218 and Escorene®UL00514, available from ExxonMobil Corporation. EVA based materials provide increased comfort for the person using an ostomy pouch made from this material. EVA is also known to exhibit the necessary characteristics for joining to another EVA member, as by heat sealing or other known sealing methods, to provide an air-tight, liquid-tight seal at the joint or seal. EVA materials can be blended to facilitate formation and film extrusion. For example, an EVA blend can have about 98% by weight EVA with about 2% anti-block and slip additives, in an EVA carrier. One suitable additive is available from A. Schulman Inc., as Polybatch® SAB-1982VA.

EMA copolymers include about 10 to about 35% of the methyl acrylate and preferably about 18.5% to about 30% by weight methyl acrylate, by weight of the copolymer. Such EMA copolymers typically have melting point temperatures of about 85° C. to 87° C. and a Shore A hardness of about 73 and Shore D hardnesses of about 20 to 25. Suitable materials are available from Arkema Inc. as Lotryl®18AM02 and from DuPont as Elvaloy®1330AC. The EMA resins can also be blended with anti-block and slip additives in an EVA carrier. One suitable material for blending is the aforementioned Polybatch® SAB-1982VA. Such a blend can have, for example EMA at about 98% by weight, with about 2% Polybatch® SAB-1982VA anti-block and slip additive.

As set forth above, other suitable seal and skin layers are formed as a blend of EVA copolymer (Escorene®FL00218 present at 49%) and PP-elastomer (Versify®2200 present at 49%) with anti-block and slip additives, and blends of EMA (Elvaloy®1330AC present at 49%) and PP-elastomer (Versify®2200 present at 49%) also with anti-block and slip additives. PP-elastomers such as Versify® from Dow, Vistamaxx® from Exxon, and Notio® from Mitsui are also suitable.

Multilayer Films

The multilayer films, such as the film 10 of FIG. 1, can be symmetrical films. That is, the layers on opposing sides of the barrier layer, namely the tie layers, inner layers and seal and skin layers are identical. The thicknesses of the various layers can also be identical. Preferably, the seven-layer film 10 has a thickness between about 60 μm and about 300 μm, and more preferably between about 90 μm and about 260 μm. The film 10 includes the barrier layer 12 having a thickness between about 25 micron (μm) and 90 μm, preferably between about 35 μm and 80 μm; the tie layers 14, 16, each tie layer having a thickness between about 2 μm and 6 μm, preferably between about 3 μm and 4 μm; the inner layers 18, 20, each inner layer having a thickness between about 5 µm and about 40 µm, preferably between about 8 µm and about 35 µm; and the skin/seal layers 22, 24, each skin/seal layer having a thickness between about 8 µm and about 70 µm, preferably between about 10 µm and about 60 µm. Preferably, the thickness of a barrier layer makes up about 30% to about 70% of the total thickness of a multi-layer film of various embodiments.

In one embodiment, the seven-layer film 10 has a thickness of about 102 µm. The barrier layer 12 is formed from about 100% wt. nylon 6/69 (Grilon® BM 13) and has a thickness of about 51 µm. Each of the tie layers 14, 16 is formed from MAH grafted EMA (Lotader®4503) and has a thickness of about 4 µm. Each of the inner layers 18, 20 is formed from EVA copolymer (EscoreneUL00514) and has a thickness of about 10 µm. Each of the skin/seal layers 22, 24 is formed from a blend comprising about 98% wt. EVA copolymer (Escorene®UL00514) and about 2% wt. anti-block and slip additive (Polybatch® SAB-1982VA), and has at thickness of about 11.5 µm.

In another embodiment, the seven-layer film 10 has a thickness of about 102 µm. The barrier layer 12 is formed from about 100% wt. nylon 6/69 (Grilon® BM 13) and has a thickness of about 38 µm. Each of the tie layers 14, 16 is formed from MAH grafted EMA (Lotader®4503) and has a thickness of about 3 µm. Each of the inner layers 18, 20 is formed from PP-elastomer (Vistamaxx® 3980FL) and has a thickness of about 12 µm. Each of the skin/seal layers 22, 24 is formed from a blend comprising about 98% wt. EVA copolymer (Escorene®UL00514) and about 2% wt. anti-block and slip additive (Polybatch® SAB-1982VA), and has at thickness of about 17 µm.

In yet another embodiment, the seven-layer film 10 has a thickness of about 102 µm. The barrier layer 12 is formed from a blend comprising about 98% wt. nylon 6/69 (Grilon® BM 13) and about 2% wt. amorphous polyamide (Grivory® G21), and has a thickness of about 51 µm. Each of the tie layers 14, 16 is formed from MAH grafted EMA (Lotader®4503) and has a thickness of about 4 µm. Each of the inner layers 18, 20 is formed from EVA copolymer (Escorene®UL00514) and has a thickness of about 10 µm. The skin/seal layer 22 is formed from a blend comprising about 98% wt. EVA copolymer (Escorene®UL00514) and about 2% wt. anti-block and slip additive (Polybatch® SAB-1982VA), and has at thickness of about 11.5 µm. Similarly, the skin/seal layer 24 is formed from a blend comprising about 98% wt. EVA copolymer (Escorene®UL00514) and about 2% wt. anti-block and slip additive (Polybatch® SAS), and has at thickness of about 11.5 µm.

In a different embodiment, the seven-layer film 10 has a thickness of about 102 µm. The barrier layer 12 is formed from a blend comprising about 98% wt. nylon 6/69 (Grilon® BM 13) and about 2% wt. amorphous polyamide (Grivory® G21), and has a thickness of about 38 µm. Each of the tie layers 14, 16 is formed from MAH grafted EMA (Lotader®4503) and has a thickness of about 3 µm. Each of the inner layers 18, 20 is formed from PP-elastomer (Vistamaxx® 3980FL) and has a thickness of about 12 µm. The skin/seal layer 22 is formed from a blend comprising about 98% wt. EVA copolymer (Escorene®UL00514) and about 2% wt. anti-block and slip additive (Polybatch® SAB-1982VA), and has at thickness of about 17 µm. Similarly, the skin/seal layer 24 is formed from a blend comprising about 98% wt. EVA copolymer (Escorene®UL00514) and about 2% wt. anti-block and slip additive (Polybatch® SAS), and has at thickness of about 17 µm.

These embodiments of the seven-layer film 10 are well suited for ostomy applications, such as an ostomy pouch.

Figure 5:
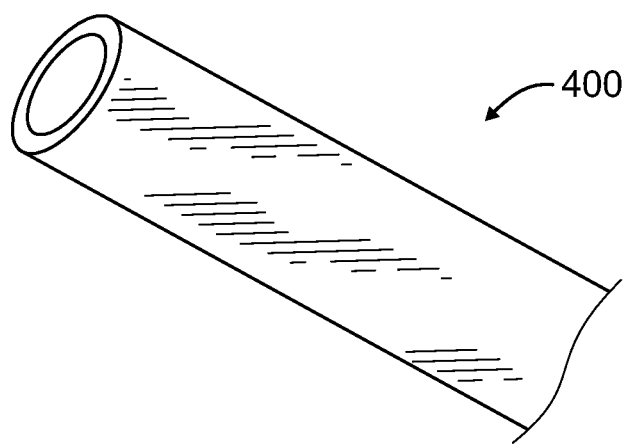
FIG. 5 is an illustration of an exemplary bowel management tube.

In another embodiment, the seven-layer film 10 has a thickness of about 254 µm. The barrier layer 12 is formed from about 100% wt. nylon 6/69 (Grilon® BM 13) and has a thickness of about 76 µm. Each of the tie layers 14, 16 is formed from MAH grafted EMA (Lotader®4503) and has a thickness of about 4 µm. Each of the inner layers 18, 20 is formed from EVA copolymer (Escorene®UL00514) and has a thickness of about 30 µm. Each of the skin/seal layer 22, 24 is formed from a blend comprising about 98% wt. EVA copolymer (Escorene®UL00514) and about 2% wt. anti-block and slip additive (Polybatch® SAB-1982VA), and has at thickness of about 55 µm. The seven-layer film 10 of this embodiment is particularly well suited for bowel management applications. For example, the multilayer film 10 can be formed into a bowel management tube 400 (FIG. 5) to provide superior odor barrier performance and excellent mechanical strength. In another embodiment, the layers 12, 14, 16, 18, 20, 22, 24 can be coextruded as a multilayer tubing.

Figure 2:
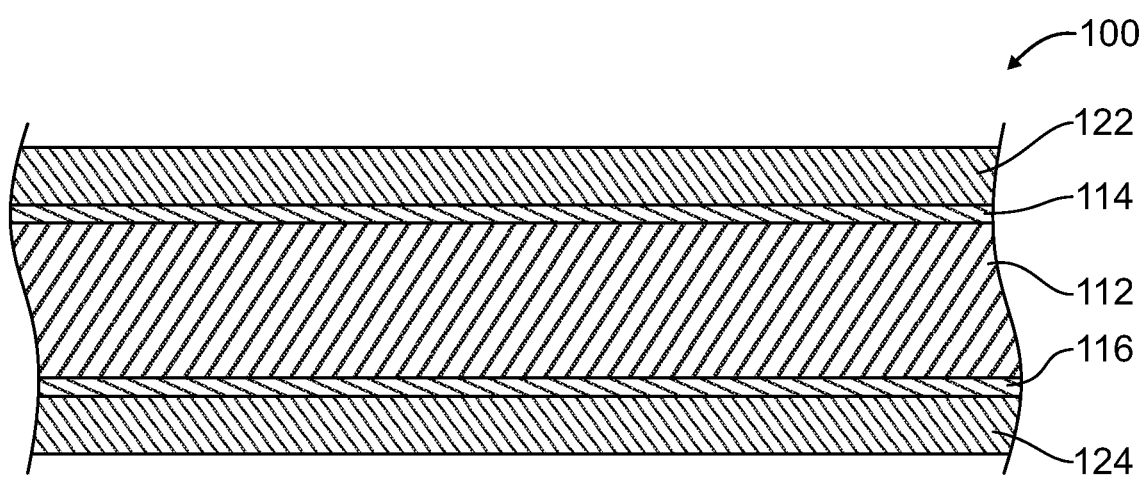
FIG. 2 is a cross-sectional illustration of a five-layer film in accordance with another embodiment.

FIG. 2 shows a five-layer film 100 according to an embodiment. The five-layer film 100 includes a barrier layer 112, two tie layers 114, 116, and two skin/seal layers 122, 124. In one embodiment, the film 100 has a thickness of about 102 µm. The barrier layer 112 is formed from about 100% wt. nylon 6/69 (Grilon® BM 13) and has a thickness of about 51 µm. Each of the tie layers 114, 116 is formed from MAH grafted EMA (Lotader®4503) and has a thickness of about 4 µm. Each of the skin/seal layers 122, 124 is formed from a blend comprising about 98% wt. EVA copolymer (Escorene®UL00514) and about 2% wt. anti-block and slip additive (Polybatch® SAB-1982VA), and has at thickness of about 21.5 µm.

In another embodiment, the five-layer film 100 has a thickness of about 102 µm. The barrier layer 112 is formed from a blend comprising about 98% wt. nylon 6/69 (Grilon® BM 13) and about 2% wt. amorphous polyamide (Grivory® G21), and has a thickness of about 51 µm. Each of the tie layers 114, 116 is formed from MAH grafted EMA (Lotader®4503) and has a thickness of about 4 µm. The skin/seal layer 122 is formed from a blend comprising about 98% wt. EVA copolymer (Escorene®UL00514) and about 2% wt. anti-block and slip additive (Polybatch® SAB-1982VA), and has at thickness of about 21.5 µm. Similarly, the skin/seal layer 124 is formed from a blend comprising about 98% wt. EVA copolymer (Escorene®UL00514) and about 2% wt. anti-block and slip additive (Polybatch® SAS), and has at thickness of about 21.5 µm.

Figure 3:
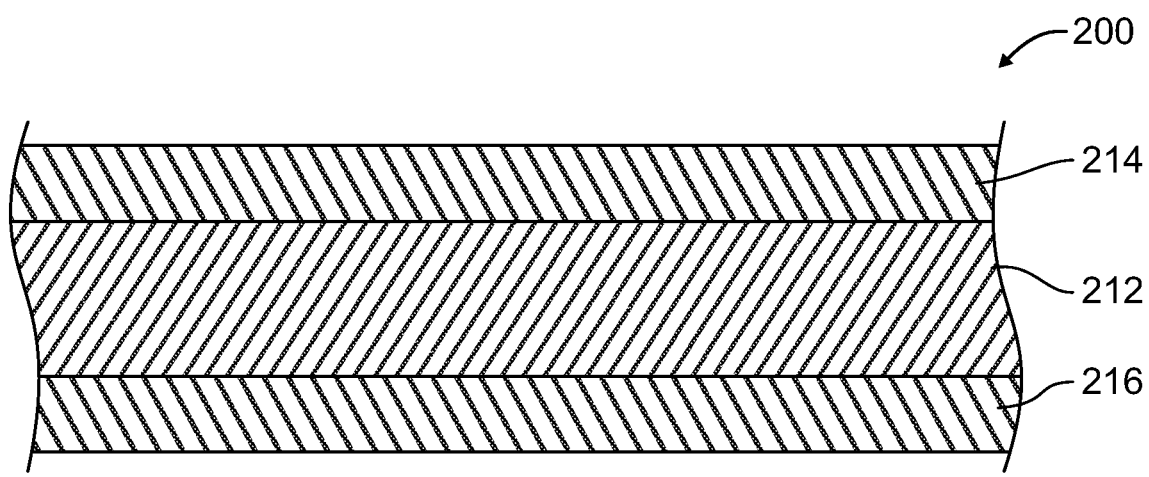
FIG. 3 is a cross-sectional illustration of a three-layer film in accordance with yet another embodiment.

FIG. 3 shows a three-layer film 200 according to an embodiment. The three-layer film 200 includes a barrier layer 212 and two skin layers 214, 216. In one embodiment, the film 200 has a thickness of about 4 mil (101.6 µm). The barrier layer 212 is formed from about 100% wt. nylon 6/69 (Grilon® BM 13), or a blend comprising about 96% wt. to 98% wt. nylon 6/69 (Grilon® BM 13) and about 2% wt. to 4% wt. amorphous polyamide (Grivory® G21), and has a thickness of about 1 mil to 2 mil (25.4 µm to 50.8 µm). Each of the skin layers 214, 216 is formed from MAH grafted EMA (Lotader®4503) and has a thickness of about 1 mil to 1.5 mil (25.4 µm to 38.1 µm).

The multilayer films according to various embodiments of the present disclosure can be formed as coextruded sheets. It is anticipated that the different thermoplastic resins used for the barrier layer, the tie layers, the inner layers, and the seal/skin layers will be fed continuously into respective extruders, melted in the extruders and transported from a feed-block or combining adaptor into a die where the different polymers, one layer over and adhering to the other, exit the die slot. Such a coextrusion process or another process for forming such a film will be recognized by those skilled in the art.

Multilayer films including a barrier layer comprising at least 60% wt. amorphous polyamide, such as those disclosed in WO 2011/056861 have provided the advantages of being environment friendly, chlorine-free films suitable for ostomy applications, such as ostomy pouches. Although such films provided suitable properties for ostomy applications, e.g. tear strength, odor and moisture barrier properties, and quietness, manufacturing of the films have been difficult due to high extrusion temperature required for amorphous nylons. For example, it was discovered that high extrusion temperatures for amorphous nylons have caused degradation of other film layers, such as layers comprising EVA. Further, amorphous polyamides have a relatively high modulus, and thus, they are difficult to cut and dull cutting knives quickly. The multilayer films of the present disclosure including a barrier layer comprising about 100% wt. nylon 6/69, which has a melting temperature comparable to that of polymeric materials of other layers and lower modulus than amorphous nylons, eliminate such manufacturing problems and facilitate the coextrusion process of the multilayer films without damaging other layers.

Further, amorphous polyamides are brittle and noisy when compared to materials having lower modulus values. Thus, a thickness of a barrier layer comprising at least 60% wt. amorphous polyamide is preferably kept under about 3 µm to provide necessary quietness and softness of the film for ostomy applications. On the other hand, the barrier layer of the present multilayer films comprising at least 90% wt. nylon 6/69 can be a much thicker barrier layer, preferably thicker than about 25 µm, to provide improved mechanical properties, while maintaining quietness and softness of the films required for ostomy applications.

Figure 4:
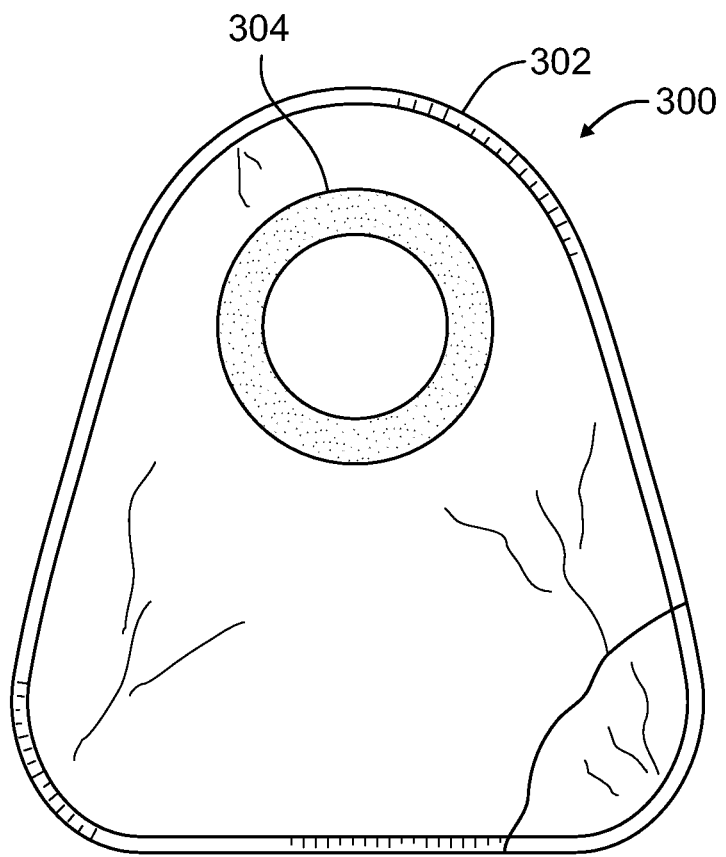
FIG. 4 is an illustration of an exemplary ostomy pouch.

The multilayer films 10, 100, 200 can be used to make, for example, an ostomy bag or pouch 300, such as that illustrated in FIG. 4. The pouch 300 is formed from two sheets of the multilayer film 10, 100, or 200 that are heat or otherwise sealed, as at 302 to one another to form an air-tight, liquid-tight pouch. An opening 304 in the pouch permits the accommodation of, for example, a surgically formed stoma (not shown) for the inflow of waste into the pouch. The configuration of such a pouch can be in accordance with the disclosure of the aforementioned U.S. Pat. No. 7,270,860 to Giori. Other configurations of pouches or other containers, as well as other uses, will be recognized by those skilled in the art.

Test Results

Several different three-layer film samples including a barrier layer comprising at least about 96% wt. nylon 6/69 and two skin layers comprising MAH grafted EMA were prepared and tested. Tensile properties in both machine direction (MD) and transverse direction (TD), and odor barrier property test results of the samples and control films (multilayer films including a barrier layer comprising at least 60% wt. amorphous polyamide) are provided in Table 1, below.

Control 1 is a multilayer film having a thickness of about 3.0 mil (76.2 µm), which includes a barrier layer comprising polyvinylidene chloride (PVDC). Control 2 is a multilayer film having a thickness of about 4.0 mil (101.6 µm), which includes a barrier layer comprising at least 60% wt. amorphous polyamide.

Sample 1 has a thickness of about 4 mil (101.6 µm). The barrier layer 212 is formed from about 100% wt. nylon 6/69 (Grilon® BM 13) and has a thickness of about 2 mil (50.8 µm). Each of the skin layers is formed from MAH grafted EMA (Lotader®4503) and has a thickness of about 1 mil (25.4 µm).

Sample 2 has a thickness of about 4 mil (101.6 µm). The barrier layer is formed from about 100% wt. nylon 6/69 (Grilon® BM 13) and has a thickness of about 1 mil (25.4 µm). Each of the skin layers is formed from MAH grafted EMA (Lotader®4503) and has a thickness of about 1.5 mil (38.1 µm).

Sample 3 has a thickness of about 4 mil (101.6 m). The barrier layer is formed from a blend comprising about 98% wt. nylon 6/69 (Grilon® BM 13) and about 2% wt. amorphous polyamide (Grivory® G21), and has a thickness of about 2 mil (50.8 µm). Each of the skin layers is formed from MAH grafted EMA (Lotader®4503) and has a thickness of about 1 mil (25.4 µm).

Sample 4 has a thickness of about 4 mil (101.6 µm). The barrier layer is formed from a blend comprising about 96% wt. nylon 6/69 (Grilon® BM 13) and about 4% wt. amorphous polyamide (Grivory® G21), and has a thickness of about 2 mil (50.8 µm). Each of the skin layers is formed from MAH grafted EMA (Lotader®4503) and has a thickness of about 1 mil (25.4 µm).

Sample 5 has a thickness of about 4 mil (101.6 µm). The barrier layer is formed from a blend comprising about 96% wt. nylon 6/69 (Grilon® BM 13) and about 4% wt. amorphous polyamide (Grivory® G21), and has a thickness of about 1 mil (25.4 µm). Each of the skin layers is formed from MAH grafted EMA (Lotader®4503) and has a thickness of about 1.5 mil (38.1 µm).

TABLE 1

TENSILE AND ODOR BARRIER TEST RESULTS FOR MULTILAYER FILMS

| | Sample 1 | Sample 2 | Sample 3 | Sample 4 | Sample 5 | Control 1 | Control 2 |
|---|---|---|---|---|---|---|---|
| Machine Direction (MD) Tensile | | | | | | | |
| Load at Break (lbf) | 8.1 | 4.7 | 8.1 | 7.7 | 5.3 | 4.4 | 4.3 |
| Tensile Strength (psi) | 4092 | 2415 | 4263 | 4005 | 2738 | 2938 | 2206 |
| Elongation (%) | 607 | 589 | 600 | 618 | 622 | 345 | 181 |
| Energy to Break (in*lbf) | 49.8 | 31.5 | 49.3 | 47.8 | 35.4 | 20.9 | 11.8 |
| Modulus (psi) | 14682 | 7959 | 17328 | 15836 | 9328 | 26252 | 25721 |

TABLE 1-continued

TENSILE AND ODOR BARRIER TEST RESULTS FOR MULTILAYER FILMS

| | Sample 1 | Sample 2 | Sample 3 | Sample 4 | Sample 5 | Control 1 | Control 2 |
|---|---|---|---|---|---|---|---|
| Transverse Direction (TD) Tensile | | | | | | | |
| Load at Break (lbf) | 8.0 | 4.7 | 8.9 | 8.6 | 5.0 | 3.5 | 3.0 |
| Tensile Strength (psi) | 4099 | 2450 | 4636 | 4550 | 2612 | 2331 | 1505 |
| Elongation (%) | 652 | 679 | 640 | 648 | 650 | 631 | 332 |
| Energy to Break (in*lbf) | 49.9 | 33.5 | 53.6 | 53.9 | 34.3 | 27.3 | 16.5 |
| Modulus (psi) | 14953 | 9018 | 17005 | 16628 | 9629 | 28109 | 23960 |
| Gas Chromatography (GC) Odor Testing | | | | | | | |
| DMDS* Breakthrough Time (minutes) | >1440 | 644 | >1440 | >1440 | >1440 | 92 | >1440 |

*DMDS—dimethyl disulfide

As shown in Table 1, the multilayer films including a barrier layer comprising at least 96% wt. nylon 6/69 (Samples 1-5) have improved tensile properties and significantly lower modulus when compared to the multilayer films including a barrier comprising PVDC or at least 60% wt. amorphous nylon (Control 1-2). Thus, the multilayer films including a barrier layer comprising at least 96% wt. nylon 6/69 provide for a stronger, softer and quieter film for ostomy applications while maintaining excellent odor barrier properties.

In the present disclosure, all percentages of constituents are by weight, unless otherwise indicated. In the present disclosure, the words "a" or "an" are to be taken to include both the singular and the plural. Conversely, any reference to plural items shall, where appropriate, include the singular. All of the concentrations noted herein as percentage are percent by weight unless otherwise noted.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

What is claimed is:

1. A multi-layer, chlorine-free film for ostomy and bowel management applications, comprising:
   a barrier layer having first and second sides, the barrier layer comprising a low melt polyamide resin having a melting temperature between about 125° C. and about 135° C. present in a concentration of about 90 percent to about 100 percent by weight (% wt.) of the barrier layer, the barrier layer being substantially impermeable to malodor causing compounds; and
   first and second outer layers, wherein each outer layer is arranged on a respective side of the barrier layer.

2. The film of claim 1, wherein each of the first and second outer layers is formed from an ethylene vinyl acetate or ethylene methyl acrylate copolymer and blends thereof, or polypropylene-based resins and blends thereof.

3. The film of claim 2, further comprising first and second tie layers, the tie layers formed from a maleic anhydride grafted resin, the resin being one or more of an ethylene-based copolymer, a propylene-based copolymer, an ethylene-octene polymer and a styrene block copolymer, wherein each tie layer contacting a respective side of the barrier layer.

4. The film of claim 3, further comprising first and second inner layers, the inner layers formed from one of an ethylene propylene copolymer (polypropylene elastomer) based resin, an ethylene-octene based resin and blends thereof, each inner layer contacting a respective tie layer, wherein the outer layers contact a respective inner layer.

5. The film of claim 1, wherein the barrier layer is formed from about 100% wt. nylon 6/69.

6. The film of claim 1, wherein the barrier layer comprises about 90% wt. to about 99% wt. nylon 6/69 and about 1% wt. to about 10% wt. amorphous polyamide.

7. The film of claim 6, wherein the barrier layer comprises about 98% wt. nylon 6/69 and about 2% wt. amorphous polyamide.

8. The film of claim 1, wherein a thickness of the barrier layer makes up about 30% to 70% of a total thickness of the film.

9. The film of claim 1, wherein a total thickness of the film is between about 60 µm and about 300 µm, and a thickness of the barrier layer is between 25 µm and 90 µm.

10. A multi-layer, chlorine-free film for ostomy and bowel management applications, comprising:
    a barrier layer having first and second sides, the barrier layer comprising a low melt polyamide resin having a melting temperature between about 125° C. and about 135° C. present in a concentration of greater than about 75 percent by weight (% wt.) of the barrier layer, the barrier layer being substantially impermeable to malodor causing compounds; and
    first and second outer layers, wherein each outer layer is arranged on a respective side of the barrier layer.

11. The film of claim 10, wherein each of the first and second outer layers is formed from an ethylene vinyl acetate or ethylene methyl acrylate copolymer and blends thereof, or polypropylene-based resins and blends thereof.

12. The film of claim 11, further comprising first and second tie layers, the tie layers formed from a maleic anhydride grafted resin, the resin being one or more of an ethylene-based copolymer, a propylene-based copolymer, an ethylene-octene polymer and a styrene block copolymer, wherein each tie layer contacting a respective side of the barrier layer.

13. The film of claim 12, further comprising first and second inner layers, the inner layers formed from one of an ethylene propylene copolymer (polypropylene elastomer) based resin, an ethylene-octene based resin and blends thereof, each inner layer contacting a respective tie layer, wherein the outer layers contact a respective inner layer.

14. The film of claim 10, wherein the barrier layer is formed from about 100% wt. nylon 6/69.

15. The film of claim 10, wherein the barrier layer comprises about 90% wt. to about 99% wt. nylon 6/69 and about 1% wt. to about 10% wt. amorphous polyamide.

16. The film of claim 15, wherein the barrier layer comprises about 98% wt. nylon 6/69 and about 2% wt. amorphous polyamide.

17. The film of claim 10, wherein a thickness of the barrier layer makes up about 30% to 70% of a total thickness of the film.

18. The film of claim 10, wherein a total thickness of the film is between about 60 μm and about 300 μm, and a thickness of the barrier layer is between 25 μm and 90 μm.

* * * * *